United States Patent [19]

Alter et al.

[11] 4,400,308

[45] Aug. 23, 1983

[54] SILVER-CONTAINING SUPPORTED CATALYSTS AND CATALYST INTERMEDIATE PRODUCTS, PROCESSES FOR THEIR PREPARATION AND THEIR USE

[75] Inventors: Eduard Alter, Lich; Ludwig Bruns, Dormagen-Straberg; Werner Volprecht, Fliesteden, all of Fed. Rep. of Germany

[73] Assignee: EC Erdolchemie GmbH, Cologne, Fed. Rep. of Germany

[21] Appl. No.: 250,816

[22] Filed: Apr. 3, 1981

[30] Foreign Application Priority Data

Apr. 12, 1980 [DE] Fed. Rep. of Germany ....... 3014091

[51] Int. Cl.$^3$ .......................... B01J 21/04; B01J 23/50
[52] U.S. Cl. .................................... 252/463; 252/454; 252/475; 252/476
[58] Field of Search ............... 252/443, 476, 463, 475, 252/454

[56] References Cited

U.S. PATENT DOCUMENTS

| 3,943,069 | 3/1976 | Antonelli et al. | 252/443 |
| 4,066,575 | 1/1978 | Winnick | 252/476 X |
| 4,207,210 | 6/1980 | Kilty | 252/476 X |
| 4,305,844 | 12/1981 | Vangermain et al. | 252/443 |

FOREIGN PATENT DOCUMENTS

| 591670 | 8/1947 | United Kingdom | 252/476 |
| 754593 | 8/1956 | United Kingdom | 252/476 |
| 1103678 | 2/1968 | United Kingdom | 252/476 |
| 1115192 | 5/1968 | United Kingdom | 252/476 |

*Primary Examiner*—Carl F. Dees
*Attorney, Agent, or Firm*—Sprung, Horn, Kramer & Woods

[57] ABSTRACT

Silver-containing supported catalyst, catalyst intermediates, processes for their preparation and the use of such catalysts in the preparation of alkaline oxides is described. By the preparatory technique of the invention there is obtained an improved catalyst which is especially useful in the preparation of alkylene oxides by oxidation of alkenes with oxygen-containing gases. The novel catalysts are characterized by a BET specific surface area of about 0.4 to about 0.5 square meters per gram and by a uniform continuous particle structure of spherical silver crystallites on a supported catalyst, which crystallites have an average diameter of 0.3 to 0.4 μm.

28 Claims, No Drawings

SILVER-CONTAINING SUPPORTED CATALYSTS AND CATALYST INTERMEDIATE PRODUCTS, PROCESSES FOR THEIR PREPARATION AND THEIR USE

The invention relates to supported catalysts and catalyst intermediate products containing silver, promoters, processes for the preparation of silver catalysts and their use for the preparation of alkylene oxides by direct oxidation of alkenes with air or oxygen-containing gases.

At present, direct oxidation of alkenes with air or with gases containing molecular oxygen, in the presence of a silver-containing catalyst, is used for the industrial preparation of alkylene oxides. Since alkylene oxides, especially ethylene oxide, are of great economic importance as base chemicals for numerous secondary products, many attempts have been made constantly to improve the efficiency of the catalysts employed. The numerous modifications which have been proposed to improve the activity and the selectivity relate to the support material used, the process for the preparation of the catalysts and the addition of promoters (R. Landau and R. E. Lidow, "Ethylene and its industrial derivatives" published by S. A. Miller and Ernest Benn, London 1963; D. J. Hucknall "Selektiv oxidations of hydrocarbons" Academic Press, London 1974; and J. of catalysis 34, 100–114 (1974)).

The operating temperature of a catalyst for the preparation of alkylene oxides is of particular importance. Catalysts which have a high activity and selectivity at a low temperature are desirable. A low operating temperature results, for example, in a longer life for the catalyst, which is of great importance for the industrial process. Furthermore, considerably less by-products, for example isomeric acetaldehyde and formaldehyde in the preparation of ethylene oxide, are formed at low temperatures, and it is thus easier to separate off these impurities during working up of the alkylene oxide to give a pure starting chemical which fulfils all requirements.

At high operating temperatures, in addition to the disadvantages already described, undesired postreactions frequently occur at the outlet of the catalyst bed. The reaction products leaving the bed can impair the efficiency of the catalyst and furthermore lead to undesired losses in production in commercially operated plants. High operating temperatures also promote the occurrence of uncontrollable hot points which, in addition to causing industrial defects, can also adversely affect the safety of the preparation process.

The operation temperature of a catalyst can be influenced by adding promoters and by the preparation process. Added amounts of oxides, hydroxides and peroxides of alkali metals and alkaline earth metals have proved to be particularly advantageous promoters (U.S. Pat. No. 2,404,438). In a series of patent applications, for example German Offenlegungsschrift No. 2,300,512, the addition of heavy alkali metals, above all, as promoters has been described. In other patent applications, for example German Auslegeschrift No. 1,920,976, barium has been particularly emphasized, among the alkaline earth metals, as a promoter.

German Offenlegungsschrift No. 2,733,688 claims a process for the preparation of silver-containing supported catalysts in which a support material is impregnated with a silver compound, the impregnated particles are activated by being at least partly converted into elementary silver and, finally, at least one of the alkali metals potassium, rubidium and cesium is precipitated onto the catalyst thus prepared. The silver-containing impregnating solution preferably contains a barium salt.

All the catalysts hitherto described have a relatively high operating temperature of 230° to 260° C.

Supported catalysts which contain silver and, if appropriate, promoters have now been found, which are prepared by a procedure in which (a) a support with a specific surface area of at most 1 m$^2$/g is impregnated with lactic acid containing silver ions and, if desired, promoter metal ions, (b) and, in a virtually oxygen-free atmosphere, the impregnated support obtained according to (a) is dried and the lactic acid, present in ionic form and in the free form, is preliminarily decomposed, the drying being carried out at a temperature of about 50° to about 120° C. and the preliminary decomposition being carried out successively in the two temperature ranges from about 140° to about 220° C. and from about 400° to about 500° C., a heating up rate of 70° to 150° C./hour being established for the transition between the two temperature ranges, and (c) the catalyst intermediate products obtained according to (b) are activated by being heated in an oxygen-containing atmosphere, the temperature being increased from at least 130° C. to at most 300° C. at a heating up rate of about 3° to about 8° C./hour, and the oxygen content being increased from about 0.4 to about 21 percent by volume in a manner such that the $CO_2$ content of the off-gas from the activation stage does not exceed 1% by volume.

The catalysts according to the invention can be catalysts with or without promoters. In the case where the catalysts according to the invention contain promoters, promoters which may be mentioned are alkaline earth metal compounds, for example compounds of calcium, strontium or barium, and/or alkali metal compounds, for example compounds of lithium, sodium, potassium, rubidium or cesium. Preferred promoters are barium compounds and/or cesium compounds. Catalysts according to the invention can contain compounds of barium or of cesium or compounds of both metals. Particularly preferred catalysts according to the invention are those which contain barium compounds and cesium compounds.

The following amounts may be mentioned as examples of amounts for the active metals and are all calculated as metals or metal ions and all relate to the total weight of the finished catalyst: an amount of about 7 to about 30% by weight, preferably 10 to 20% by weight and particularly preferably 12 to 18% by weight, for silver; if alkaline earth metal compounds are present as promoters, an amount of about 0.05 to about 0.5% by weight, preferably 0.07 to 0.3% by weight and particularly preferably 0.08 to 0.15% by weight, for these; and in the case where alkali metals are present as promoters, an amount of about 0.001 to about 0.03% by weight, preferably 0.003 to 0.02% by weight and particularly preferably 0.004 to 0.01% by weight, for these; if alkaline earth metals and alkali metals are present together as promoters, they can be present, independently of one another, in the amounts given in each case, for these compounds.

Support materials which may be mentioned for the catalysts according to the invention are porous, heat-stable catalyst support materials which are inert under the conditions for the preparation of the catalyst and for the use of the catalyst. The support material has a macroporous structure with a specific surface area of at most 1 m²/g, for example 0.001 to 1 m²/g, preferably 0.002 to 0.1 m²/g and particularly preferably 0.005 to 0.05 m²/g. The porosity of the support material is, for example, 40 to 70%, preferably 45 to 60%. For the pore diameter, a range of, for example, 100 to 1,500 μm may be mentioned. Possible support materials with the physical properties mentioned are those of natural or synthetic origin, for example α-aluminum oxide, silicon carbide, synthetic or natural zeolites, magnesium oxide, zirconium oxide or ceramic materials, preferably α-aluminum oxide.

The invention furthermore relates to a process for the preparation of supported catalysts which contain silver and, if appropriate, promoters, by impregnating a support with a solution containing silver and, if appropriate, promoter metals and then drying and calcining the support, which is characterized in that (a) a support with a specific surface area of at most 1 m²/g is impregnated with lactic acid containing silver and, if desired, promoter metal ions in a manner which is in itself known, (b) the impregnated support obtained according to (a) is dried in a virtually oxygen-free atmosphere at about 50° to about 120° C. and the lactic acid, present in ionic form or in the free form, is preliminarily decomposed, successively in the two temperature ranges from about 140° to about 220° C. and from about 400° to about 500° C., in a virtually oxygen-free atmosphere, a heating up rate of 70° to 150° C. per hour being established for the transition between the two temperature ranges, and (c) the catalyst intermediate product obtained according to (b) is activated by being heated in an oxygen-containing atmosphere, the temperature being increased from at least 130° to at most 300° C. at a heating up rate of about 3° to about 8° C./hour and the oxygen content being increased from about 0.4 to about 21% by volume in a manner such that the $CO_2$ content of the off-gas from the activation stage does not exceed 1% by volume.

As a support for the catalyst preparation process according to the invention, there may be mentioned, for example, one of the supports described above, with the physical properties described above. α-aluminum oxide with the properties described above is preferably employed as the support.

As the lactic acid, there may be employed the racemate, which contains the two optical antipodes, in each case in the same amount, or a lactic acid which contains one of the optical antipodes in excess. It is preferable to use a lactic acid which, in addition to containing the racemate, contains one of the optical antipodes in excess. A lactic acid which contains at least 50% by weight of an optical antipode, preferably at least 50% by weight of the L(+)-form and particularly preferably at least 80% by weight of the L(+)-form, the remainder in each case consisting of the racemate of the two optically active forms, may be mentioned as an example of this preferred form of lactic acid.

The lactic acid employed, according to the invention, for impregnating the catalyst support contains silver in the form of silver ions. Introduction of silver oxide, silver carbonate or separately prepared silver lactate into the lactic acid may be mentioned as an example of the preparation of such a silver-containing lactic acid. Other silver compounds which can be decomposed under the influence of heat can, of course, also be used here. It is preferable to introduce silver oxide, and particularly preferably freshly precipitated silver oxide, into the lactic acid. The lactic acid used for the impregnation contains, for example, 30 to 45% by weight, preferably 35-40% by weight, of silver ions, relative to the total amount of impregnating liquid. If appropriate, the desired content of silver ions can be established before the impregnation by adding distilled water to the impregnating liquid to reach the desired amount. The silver-containing lactic acid is prepared at a temperature of, for example, 40° to 70° C. When the addition of the silver compound has ended, it is expedient also to add an amount of about 1 ml of 30% strength by weight hydrogen peroxide solution/100 g of silver ions to the lactic acid.

In the case where alkaline earth metal ions and/or alkali metal ions are added as promoters, an addition of hydroxides or carbonates of one or more alkaline earth metals and/or alkali metals may be mentioned. For the alkaline earth metals, the following compounds may be mentioned as examples: calcium hydroxide, calcium carbonate, strontium hydroxide, strontium carbonate, barium hydroxide and barium carbonate, preferably barium hydroxide or barium carbonate. Examples of alkali metal compounds which may be mentioned are: lithium hydroxide, lithium carbonate, sodium hydroxide, sodium carbonate, potassium hydroxide, potassium carbonate, rubidium hydroxide, rubidium carbonate, cesium hydroxide and cesium carbonate, preferably cesium hydroxide or cesium carbonate. An amount of about 0.5 to 3 g, preferably 1 to 2 g, per 100 g of 100% strength lactic acid may be mentioned as an example of an amount in the case of the alkaline earth metal compounds. For the alkaline metal compounds, an amount of, for example, 30 to 300 mg, preferably 70 to 150 mg, per 100 of 100% strength lactic acid may be mentioned.

The amount of lactic acid containing silver and, if appropriate, the promoter metals which is employed and the amounts of the active metals contained therein depend, of course, on the desired amount of active metals on the finished catalyst, within the context of the abovementioned ranges for the individual metals and also according to the porosity of the catalyst support employed. However, these relationships can be determined in simple preliminary experiments. The volume of lactic acid solution employed for the impregnation is chosen such that the catalyst support is completely impregnated, but only a little impregnating liquid drips off the impregnated catalyst after the impregnation. An amount of about 5 to 30% by volume, preferably 10 to 20% by volume, of the total lactic acid solution employed may be mentioned as an example of the amount of lactic acid solution which drips off the impregnated support.

In a preferred variant of the process according to the invention, one can add soluble, readily decomposable, non-reducing organic compounds, such as sugar-alcohols (sorbitol or mannitol), polyhydroxy acids, sucrose, starch or trimellitic acid, preferably sucrose, to the lactic acid containing silver and, if appropriate, promoter metals. These organic compounds mentioned are added in amounts of, for example, about 30 to about 45 g/100 g of 100% strength lactic acid.

The sequence of the addition of the individual components of the impregnating liquid can be, for example, as follows: initial introduction of the lactic acid into the vessel, if appropriate introduction of the alkaline earth metal compound, if appropriate introduction of the alkali metal compound, introduction of the silver compound, if appropriate addition of the hydrogen peroxide, and if appropriate addition of the organic compound described. However, the components mentioned can also be introduced into the initially introduced lactic acid in any other sequence.

A catalyst support described above is impregnated, with the impregnating liquid obtained in the manner described, by being immersed in the solution once or several times. The excess of impregnating liquid described is allowed to drip off freely, and the impregnated support is then introduced into a circulating air oven.

A virtually oxygen-free atmosphere is maintained in this circulating air oven. An atmosphere which contains at most 100 ppm by volume of $O_2$, for example 1 to 100, preferably 1 to 20, ppm by volume, may be mentioned as a virtually oxygen-free atmosphere. Nitrogen, carbon dioxide or noble gases, preferably nitrogen, which are oxygen-free or in which the oxygen content is within the range mentioned, can be used, for example, as the inert gas for the virtually oxygen-free atmosphere.

A temperature of about 50° to about 120° C., preferably 90° to 120° C. and particularly preferably 100° to 110° C., is established in the circulating air oven described, in order to dry the impregnated support. The duration of the drying operation depends on the amount of impregnated support, the amount of water in the impregnating liquid, the amount of the circulating air stream and the level of the temperature, within the range given. This time can be in the range from about 1 to about 4 hours.

Thereafter, the impregnated and dried catalyst support is subjected to preliminary decomposition of the organic constituents, likewise in a virtually oxygen-free atmosphere. For this, the temperature is first increased to the range from about 140° to about 220° C., preferably 140° to 160° C. and particularly preferably 145° to 155° C., and is kept in this range for about ½ to about 2 hours. A second preliminary decomposition temperature is then established at a heating up rate of 70° to 150° C., preferably 90° to 110° C., per hour. This second temperature is, for example, in the range from about 400° to about 500° C., preferably 430° to 470° C., and is maintained for about ½ to about 2 hours, as is the first preliminary decomposition temperature. The mode of action of the two separate temperature ranges described has not yet been conclusively investigated. However, it can be assumed that gentle decomposition of the organic material is started in the first of the preliminary decomposition temperature ranges given, the growing together of silver crystals to form relatively large units being largely avoided. In the second of the preliminary decomposition temperature ranges mentioned, further decomposition of the organic material and removal of the volatile pyrolysis products can be assumed. In the case where promoter metals are present in the catalyst, it can also be assumed that solid phase reactions take place between the promoter metal compounds and the silver in the second of the temperature ranges mentioned.

After this preliminary decomposition according to the invention, the catalyst intermediate product thereby obtained still contains 0.5 to 8% by weight, preferably 1 to 8 and particularly preferably 2 to 5% by weight, of carbon, relative to the total weight of the catalyst intermediate product.

After the preliminary decomposition described, the catalyst intermediate product is activated by being heated in an oxygen-containing atmosphere. For this heating operation, the catalyst intermediate product is first brought to a temperature of at most 130° C. in the virtually oxygen-free atmosphere and then treated at a temperature rising continuously from at least 130° C. to at most 300° C., in the presence of oxygen, a heating up rate of about 3° to about 8° C. per hour being maintained. The rise in temperature described is preferably effected from at least 140° to at most 260° C. and particularly preferably from at least 150° to at most 240° C.

At the start of the heating up program described, the virtually oxygen-free atmosphere is replaced by an atmosphere initially containing about 0.4% by volume of oxygen, it being possible for the remainder to make up to 100% by volume to consist, for example, of the abovementioned inert gases. This oxygen content in the activation atmosphere is then slowly increased from the approximately 0.4% by volume mentioned up to about 21% by volume in a manner such that the $CO_2$ content of the off-gas of this activation stage does not exceed 1% by volume. The duration of this activation according to the invention can be deduced from the heating up rate and the temperature range chosen, and is, for example, 12 to 30 hours.

The preliminary decomposition and activation according to the invention can in each case be carried out under normal pressure, reduced pressure or increased pressure, independently of one another. A range from 0.1 to 50 bars, preferably 1–20 bars and particularly preferably 5 to 15 bars, may be mentioned by way of example.

In the process according to the invention, it is not necessary to carry out the preliminary decomposition and the activation to give the finished catalyst immediately one after the other. After passage through the second preliminary decomposition temperature range in a virtually oxygen-free atmosphere, it is thus possible, for example, for the catalyst intermediate product thereby obtained to be cooled to about 70° to 80° C. under a virtually oxygen-free atmosphere and then to be removed, as an intermediate product, from the circulating air oven. As described, this catalyst intermediate product contains about 0.5 to about 8% by weight, preferably 1 to 8 and particularly preferably 2 to 5% by weight, of carbon, relative to the total weight of this intermediate product. This intermediate product can be stored as desired without loss in the catalytic activity of the active silver catalyst which can be prepared therefrom. The intermediate product is activated before being used to give the final catalyst. This activation can be effected, for example, in the circulating air oven described, under the conditions described.

However, it is also possible to activate the catalyst intermediate product in the reactor in which the catalyst which has been finished after activation is employed for the predetermined catalytic reaction, for example in a reactor for the preparation of an alkylene oxide, as long as such a reactor enables the abovementioned activation conditions in respect of temperature program and metering of oxygen to be maintained. This procedure last-mentioned for activating the catalyst intermediate product is preferred.

For example, the catalyst intermediate product, if appropriate after prolonged intermediate storage, can be filled into the known tube system of a fixed bed reactor for the preparation of the ethylene oxide. The intermediate product is then warmed to at least 130° C. under a virtually oxygen-free stream of inert gas. Heating can be effected by the stream of inert gas, but it can also be assisted by a heat exchanger medium circulating around the tubes. The temperature rise which has already been described is then effected at the heating up rate described, and an initial oxygen concentration of about 0.4% by volume is established. The $CO_2$ content of the off-gas stream from the reactor is continuously monitored and, according to the invention, should not exceed 1% by volume. The oxygen content in the reactor inlet gas is then increased to about 21% by volume in the manner described, the above $CO_2$ content being maintained. When, after the upper temperature value in the activation stage has been reached, the $CO_2$ content of the reactor off-gas has fallen to a value of less than 0.3% by volume, for example to about 0.1% by volume, activation of the catalyst is stopped. The temperature in the reactor is then lowered to the temperature required for the preparation of an alkylene oxide, for example the temperature required for the preparation of ethylene oxide, and the preparation of alkylene oxide, for example ethylene oxide, is started by passing the gas mixture, which is known to the expert, for the preparation of an alkylene oxide into the catalyst bed.

The invention thus also relates to intermediate products for supported catalysts containing silver and, if appropriate, promoters, which are characterized by the steps, according to the invention and described above, of impregnation, drying, preliminary decomposition and subsequent cooling in a virtually oxygen-free atmosphere to a temperature of about 70° to 80° C.

The invention likewise relates to a process for the preparation of such catalyst intermediate products which, in the same way, is characterized by the steps, according to the invention and described above, of impregnation, drying, preliminary decomposition and cooling under a virtually oxygen-free atmosphere to about 70° to 80° C.

Compared with the catalysts obtained by customary preparation processes, the catalysts according to the invention display significant differences in their specific surface area, the morphology of the silver surface and the particle size of the silver crystallites. Thus, the specific surface area, measured by the BET process (J. Am. Chem. Soc. 60, 309-316 (1938)), is about 0.4 to 0.5 m$^2$/g, compared with a specific surface area of less than 0.1 m$^2$/g in the case of catalysts which have been prepared by customary processes. Microscopic examination shows a uniform, continuous particle structure with spherical silver crystallites which have an average diameter of 0.3 to 0.4 μm in the case of catalysts according to the invention, whilst the morphology of the silver surface in the case of catalysts which have been obtained by the customary processes shows a vitreous coating with silver crystallites which have an average diameter of 0.7 to 2 μm.

The catalysts according to the invention can be used, for example, for the preparation of alkylene oxides by vapour phase oxidation of olefins with air or with other gases containing molecular oxygen. Examples of alkylene oxides which may be mentioned are ethylene oxide, propylene oxide, 1,2-butylene oxide or 2,3-butylene oxide, preferably ethylene oxide. Examples which may be mentioned of olefins which can be employed for this reaction are ethylene, propylene, 1,2-butylene or 2,3-butylene, preferably ethylene. The invention thus also relates to the use of catalysts according to the invention for the described preparation of alkylene oxides.

This use according to the invention is particularly advantageous because of the surprisingly high activity and high selectivity with respect to the alkylene oxide yield. Thus, the operating temperature for the preparation of ethylene oxide using the catalysts according to the invention can be adjusted to 160° to 230° C., preferably 180° to 220° C., whilst customary operating temperatures in processes according to the state of the art are 230° to 260° C. These advantageously low temperatures may be applied as well to the so-called air-process, wherein oxygen and nitrogen as a diluent come from the used air, as to the so-called oxygen-process, wherein enriched or pure oxygen is used and a different inert diluent, e.g. methane, is added. Gas mixtures for the mentioned processes may contain the following constituents:

$C_2H_4$: 5-40% by volume,
$O_2$: 4-9% by volume,
$CH_4$: 0-60% by volume and
$N_2$: 0-85% by volume.

In addition, there may be present smaller amounts of further inerts, e.g. carbon dioxide of from 0 to 5% by volume and an usual inhibitor, e.g. 1 to 5 ppm of 1,2-dichloroethane.

Even at a temperature as low as 160° C., preferably 180° C., and slightly above, as already mentioned, transformation rates of ethylene are at least 6%, e.g. 6-9%, per passage whereby selectivities of ethylene oxide of at least 79%, e.g. 79 to 82%, of the transformed ethylene are reached.

A further advantage of the inventive catalysts is the fact that their selectivity percentage is kept on the high starting level of 79 to 82%, while known silver-containing catalysts, even if they start with a selectivity percentage of approximately 80%, show a remarkable decrease to about 72 to 76% within the first 2 to 3 months and only when keeping their selectivity at this lower level. Thus, inventive catalysts showed a constant selectivity within the range of 79 to 82% over a period of three months, after which time tests were interrupted without any sign of decreasing selectivity.

As a result of the lower operating temperature, the formation of undesired by-products is suppressed when the catalysts according to the invention are used. The formation of hot points in the catalyst bed is likewise suppressed, the safety of the process for the preparation of alkylene oxides simultaneously being promoted.

The preliminary decomposition and activation, according to the invention, of the catalyst according to the invention proceed under exceptionally mild conditions, which lead to the particular properties described for the catalysts according to the invention. In contrast, in the conventional processes of uncontrolled decomposition and activation of silver-containing supported catalysts very high temperatures which occur at points because of the combustion of carbon to carbon dioxide, which proceeds as a highly exothermic reaction and is catalyzed in an uncontrolled manner by the silver present, could not be avoided because of the absence of temperature control and oxygen control. Such irregularities in the preparation of the catalyst have, however, a very adverse effect on the structure of the silver crystals, which is responsible for the catalytic activity.

There is another significant advantage of the present invention in the preferred process variant in which, utilizing the catalyst intermediate product according to the invention, this intermediate product is activated in the alkylene oxide reactor: the very critical handling of activated catalysts, which is known to any expert, for example during storage, during transportation or during filling into the reactor, is dispensed with. At the same time, all the possible irreversible adverse effects of handling activated catalysts are excluded, so that, in the preferred process variant, catalysts according to the invention are ready for their intended use in a completely active state which has been impaired by nothing.

EXAMPLE 1

170 g of a 5% strength by weight aqueous NaOH solution are added to 190 g of a 16.7% strength by weight aqueous $AgNO_3$ solution. The precipitated silver oxide is washed until free from nitrate, and is separated from the water in a separator. 321 mg of barium hydroxide in the form of $Ba(OH)_2.8H_2O$ are introduced, whilst stirring, into 22 g of initially introduced 100% strength lactic acid, which consists of the optically active L(+)-configuration to the extent of 80%. 20 mg of cesium carbonate are then introduced, likewise whilst stirring. The silver oxide precipitate is introduced into the lactic acid thus prepared. The temperature of the solution is kept between 40° and 70° C. Finally, about 1 ml of $H_2O_2$ (30% strength) is added, whilst stirring. The clear yellow-coloured solution is adjusted to a silver content of 38% by weight by adding water. 105 g of $\alpha$-$Al_2O_3$ are impregnated with the resulting silver lactate solution. After excess silver lactate solution has dripped off, the impregnated support is dried in a circulating air oven under nitrogen at about 80° C. for 2 hours. The residual oxygen content remains less than 100 ppm.

After drying the support, the temperature is increased to 220° C. in the course of 2 hours and is then kept at this level for 2 hours. Thereafter, the support is heated to 450° C. at a heating up rate of 100° C./hour, whilst still under nitrogen, and this temperature is likewise maintained for 1 hour and is then reduced to 70°-80° C. This intermediate product, which still contains about 3% by weight of carbon, is filled into the experimental reactor. The reactor is charged with nitrogen (space/time velocity: 200 to 1,000 l/hour) and the temperature is increased to 150° C. via the heating medium. The residual oxygen in the nitrogen remains less than 100 ppm.

Oxygen is now added, by metering in with the inert gas, in an amount such that the oxygen inlet concentration is 0.4 to 6% by volume. The formation of $CO_2$ is followed analytically. The $CO_2$ content must not exceed 1% by volume. The temperature is increased by about 5° C./hour, according to the $CO_2$ content. The amount of oxygen metered in is likewise increased by about 1% by volume/hour. After a final temperature of 240° C. and an oxygen content of 21% by volume have been reached, the activation of the intermediate product is ended 4 to 6 hours after the $CO_2$ content has fallen to less than 0.1% by volume. The temperature in the reactor is lowered to 160° C. and the gas mixture required for the reaction to give ethylene oxide is passed over the catalyst. After a conditioning period of about 48 hours, the catalyst thus prepared achieves its final activity and selectivity. The catalyst thus prepared is referred to as A. The experimental results are in Table 1.

EXAMPLE 2

A catalyst is prepared as in Example 1. In addition to barium and cesium, 8 g of sucrose are also added to the lactic acid. The catalyst is referred to as B.

EXAMPLE 3

(For Comparison)

An impregnated catalyst support is prepared as in Example 1. Decomposition of the impregnated support is carried out in a circulating air oven in the presence of air. The support is heated to 400° C. at a heating up rate of 100° C./hour and is kept at this temperature for 1 hour and then cooled. The catalyst is referred to as C.

EXAMPLE 4

(Use Example)

The laboratory experimental reactor consists of an oil-heated glass tube which has a double-wall jacket and an internal diameter of 50 mm and a length of 1,000 mm, 100 mm of which are filled with an inert support material, and which serves as a preliminary heating zone. The laboratory experiments were carried out under atmospheric pressure. The product gas stream from the reactor was continuously monitored analytically by a process gas chromatogram. The space/time velocity was: 250 parts by volume of gas per part by volume of catalyst and hour. The gas mixture employed for the gas phase oxidation on the catalyst consists of: 30% by volume of $C_2H_4$, 8% by volume of $O_2$, 50% by volume of $CH_4$ and 12% by volume of $N_2$+inert substances. 1 to 2 ppm of 1,2-dichloroethane were added, as an inhibitor, to the gas mixture employed.

TABLE 1

| Catalyst | Temperature (°C.) | EOX (% by volume)* | Selectivity |
|---|---|---|---|
| A | 160 | 1.2 | 81 |
| A | 180 | 1.7 | 80.5 |
| A | 200 | 2.0 | 80.0 |
| A | 205 | 2.08 | 80.0 |
| B | 160 | 1.5 | 81.5 |
| B | 180 | 2.0 | 80.9 |
| B | 190 | 2.3 | 80.4 |
| B | 200 | 2.5 | 80.6 |
| C | 240 | 2.2 | 79.0 |

After operation for 3 months at the various temperatures indicated, the catalysts showed no loss in activity.
*EOX = ethylene oxide content of the gas stream leaving the reactor.

What is claimed is:

1. A supported catalyst containing silver characterized in that:
   (a) It has a BET specific surface area of 0.4 to 0.5 square meters per gram;
   (b) has a uniform continuous particle structure with spherical silver crystallites thereon which have an average diameter of 0.3 to 0.4 $\mu$m.

2. A supported catalyst according to claim 1, containing between 7 and about 30 percent by weight silver.

3. A supported catalyst according to claim 1, wherein said support comprises an alumina support.

4. A supported catalyst according to claim 3, wherein said alumina is $\alpha$-alumina.

5. A supported catalyst according to claim 3, containing 0.05 to 0.5 percent by weight of an alkaline earth metal compound.

6. A supported catalyst according to claim 5, containing 0.07 to 0.3 percent by weight of an alkaline earth metal compound.

7. A supported catalyst according to claim 3, containing 0.001 to 0.03 percent by weight of alkali metal.

8. A supported catalyst according to claim 7, containing 0.003 to 0.002 percent by weight alkali metal.

9. A supported catalyst according to claim 3, wherein said support itself is a porous heat stable catalyst support.

10. A supported catalyst containing silver prepared by a process comprising:
   (a) impregnating a support whose specific surface area is at most 1 square meter per gram with lactic acid containing silver ions;
   (b) in a virtually oxygen-free atmosphere, drying the so-impregnated support and preliminarily decomposing lactic acid present in ionic or free form by heating the same at a temperature of about 50° to about 120° C., the preliminary decomposition being carried out successively in two temperature ranges from about 140° to 220° C. and from about 400° to 500° C., employing a heating up rate of 70° to 150° C. per hour for the heat-up rate between the two temperature ranges; and
   (c) activating the intermediate product of step (b) by heating the same in an oxygen-containing atmosphere at a temperature of at least 130° C. to at most 300° C. at a heating up rate of about 3° to about 8° C. per hour, the oxygen content being increased from about 0.4 to about 21% by volume in such a manner that the $CO_2$ content of the off-gas from the activation does not exceed 1% by volume.

11. A supported catalyst according to claim 10, wherein said support comprises alumina.

12. A supported catalyst according to claim 11, wherein said lactic acid contains barium and cesium as promoters.

13. A supported catalyst according to claim 11, wherein said lactic acid contains a soluble readily decomposable non-reducing compound.

14. A supported catalyst according to claim 13, wherein said soluble readily decomposable non-reducing organic compound is a sugar alcohol, or polyhydroxy acid.

15. A supported catalyst according to claim 14, wherein said sugar alcohol or polyhydroxy acid is present in said lactic acid in an amount of 30 to about 45 grams per 100 grams based upon 100% strength lactic acid.

16. A supported catalyst according to claim 11, wherein said preliminary combustion is effected until the carbon content of the preliminary decomposed product is between 0.5 to 8 percent by weight relative to the total weight of the catalyst intermediate product.

17. A supported catalyst according to claim 11, wherein a heating at a temperature from 140° to about 220° C. is effected for a period of time between ½ hour and 2 hours and a heating at a temperature in the range of 400° to 500° C. is effected for between ½ to about 2 hours.

18. An intermediate product for the preparation of a supported catalyst containing silver prepared by a process comprising the steps of:
   (a) impregnating a support whose specific surface area is at most 1 square meter per gram with lactic acid containing silver ions; and
   (b) drying the so-impregnated support in a virtually oxygen-free atmosphere at a temperature of 50° to about 120° C. to preliminarily decompose the lactic acid present in ionic form or in the free form and thereafter continuing preliminary decomposition by subjecting the so-dried composition to temperatures in two temperature ranges, from 140° to 200° C. and from 400° to about 500° C., the heating up range between the 140°–220° C. and 400° to 500° C. range being at a rate of 70° to 150° C. per hour and thereafter cooling the intermediate product in a virtually oxygen free atmosphere to about 70° to about 80° C. or below.

19. The intermediate product of claim 18, whose carbon content is 0.5 to 8 percent by weight.

20. A process for the preparation of a supported catalyst containig silver which comprises the steps of:
   (a) contacting a support whose specific surface area is at most 1 square meter per gram with lactic acid containing silver;
   (b) drying the so-impregnated support in a virtually oxygen-free atmosphere at about 50° to about 120° C. and preliminarily decomposing the lactic acid present in ionic form or in free form by subjecting the same successively to two temperature ranges, one from about 140° to 220° C. and a second from 400° to 500° C., in a virtually oxygen-free atmosphere, the heating up rate from the temperature range of 140°–220° C. to the temperature range of 400° to 500° C. being 70° to 150° C. per hour;
   (c) activating the product obtained by step (b) by heating the same in an oxygen-containing atmosphere, the temperature being increased from at least 130° C. to at most 300° C. employing a heating-up rate of about 3° to about 8° C. per hour with increasing oxygen concentration from 0.4 to about 21 percent by volume in such a manner that the $CO_2$ content of the off-gas from the activation does not exceed 1% by volume.

21. A process according to claim 20, wherein said support comprises alumina.

22. A process according to claim 11, wherein the lactic acid contains barium and cesium.

23. A process according to claim 21, wherein the lactic acid employed is an optically active form of lactic acid.

24. A process according to claim 21, wherein at least 50% of the lactic acid employed consists of the L (+) form while the remainder is in the form of the racemate.

25. A process according to claim 21, wherein the activation is effected under pressure in a reactor employed for the preparation of an alkaline oxide.

26. A process according to claim 25, wherein the pressure within the reactor is 10–15 bars.

27. A process according to claim 21, wherein the lactic acid contains a soluble readily decomposible non-reducing organic compound.

28. A process for the preparation of catalyst intermediate product which comprises:
   (a) impregnating an alumina support whose specific surface area is at most 1 square meter per gram with lactic acid containing silver;
   (b) drying the so-impregnated product in a virtually oxygen-free atmosphere at about 50° to about 120° C. and preliminarily decomposing the lactic acid, present in ionic form or in the free form, by subjecting it successively to temperatures in two different ranges, one of which is 140° to 220° C. and the second of which is 400° to 500° C., in a virtually oxygen-free atmosphere, employing a heat up rate from the 140°–220° C. range to the 400°–500° C. range of 70° to 150° C. per hour and thereafter cooling the so-heated support in a virtually oxygen-free atmosphere to about 70° to 80° C. or below.

* * * * *

UNITED STATES PATENT AND TRADEMARK OFFICE
CERTIFICATE OF CORRECTION

PATENT NO. : 4,400,308

DATED : August 23, 1983

INVENTOR(S) : Eduard Alter et al

It is certified that error appears in the above-identified patent and that said Letters Patent is hereby corrected as shown below:

Col. 12, line 63          Delete "220°" and insert --200°--

Signed and Sealed this

Sixth Day of December 1983

[SEAL]

Attest:

GERALD J. MOSSINGHOFF

*Attesting Officer*          *Commissioner of Patents and Trademarks*